(12) United States Patent
McAnally et al.

(10) Patent No.: US 10,527,534 B2
(45) Date of Patent: Jan. 7, 2020

(54) DETERMINING A VIBRATION RESPONSE PARAMETER OF A VIBRATORY ELEMENT

(71) Applicant: Micro Motion, Inc., Boulder, CO (US)

(72) Inventors: Craig B McAnally, Thornton, CO (US); Andrew S Kravitz, Frederick, CO (US)

(73) Assignee: Micro Motion, Inc., Boulder, CO (US)

( * ) Notice: Subject to any disclaimer, the term of this patent is extended or adjusted under 35 U.S.C. 154(b) by 241 days.

(21) Appl. No.: 15/529,180

(22) PCT Filed: Mar. 3, 2015

(86) PCT No.: PCT/US2015/018472
§ 371 (c)(1),
(2) Date: May 24, 2017

(87) PCT Pub. No.: WO2016/099591
PCT Pub. Date: Jun. 23, 2016

(65) Prior Publication Data
US 2017/0336309 A1 Nov. 23, 2017

Related U.S. Application Data

(60) Provisional application No. 62/094,255, filed on Dec. 19, 2014.

(51) Int. Cl.
*G01N 9/00* (2006.01)
*G01H 13/00* (2006.01)
(Continued)

(52) U.S. Cl.
CPC .......... *G01N 9/002* (2013.01); *G01H 13/00* (2013.01); *G01N 11/16* (2013.01); *G01N 29/024* (2013.01);
(Continued)

(58) Field of Classification Search
CPC .. G01N 9/002; G01N 11/16; G01N 2009/006; G01N 2291/02818; G01N 2291/0427; G01N 29/036; G01N 29/222
See application file for complete search history.

(56) References Cited

U.S. PATENT DOCUMENTS 4,922,745 A * 5/1990 Rudkin .................. G01N 9/002
73/32 A
6,711,942 B2 * 3/2004 Getman ................. G01N 9/002
73/54.25
(Continued)

FOREIGN PATENT DOCUMENTS

JP 2011209259 A 10/2011
WO 2014175902 A1 10/2014

OTHER PUBLICATIONS

Boudjiet M T et al: New characterization methods for monitoring small resonant frequency variation: Experimental tests in the case of hydrogen detection with uncoated silicon microcantilever-based sensors; Sensors and Actuators B: Chemical: International Journal Devoted to Research and Development of Physical and Chemical Transducers, vol. 199, Apr. 13, 2014 (Apr. 13, 2014), pp. 269-276, XP0288505637, ISSN: 0925-4005, DOI:10.1016/J.SNB.2014.03. 098.
(Continued)

*Primary Examiner* — David A Rogers
(74) *Attorney, Agent, or Firm* — The Ollila Law Group LLC

(57) ABSTRACT

A method (900, 1000) of determining a vibration response parameter of a vibratory element (104) is provided. The method (900, 1000) includes vibrating the vibratory element (104) at a first frequency with a first drive signal, receiving a first vibration signal from the vibratory element (104) vibrated at the first frequency, measuring a first phase difference, the first phase difference being a phase difference
(Continued)

between the first drive signal and the first vibration signal. The method (900, 1000) also includes vibrating the vibratory element (104) at a second frequency with a second drive signal, receiving a second vibration signal from the vibratory element (104) vibrated at the second frequency, measuring a second phase difference, the second phase difference being a phase difference between the second drive signal and the second vibration signal. The method (900, 1000) further includes using the first phase difference and the second phase difference to determine at least one of a phase difference, and a frequency of the vibratory element (104).

16 Claims, 10 Drawing Sheets

(51) Int. Cl.
*G01N 11/16* (2006.01)
*G01N 29/024* (2006.01)
(52) U.S. Cl.
CPC ......... *G01N 2009/006* (2013.01); *G01N 2291/02818* (2013.01)

(56) References Cited

U.S. PATENT DOCUMENTS

| | | | | |
|---|---|---|---|---|
| 7,426,853 B2* | 9/2008 | Kubota | ............... | G01N 29/022 73/64.53 |
| 8,220,313 B2* | 7/2012 | Lopatin | ............... | G01F 23/296 73/32 R |
| 8,763,443 B2* | 7/2014 | Hussain | ............... | G01N 9/002 73/32 A |
| 8,915,147 B2* | 12/2014 | Kolahi | ............... | G01F 1/74 73/861.355 |
| 9,354,202 B2* | 5/2016 | Medin | ............... | G01N 29/022 |
| 9,846,115 B2* | 12/2017 | Urey | ............... | G01N 29/022 |
| 2002/0040592 A1* | 4/2002 | Getman | ............... | G01N 9/002 73/54.25 |
| 2005/0034537 A1* | 2/2005 | Henry | ............... | G01F 1/8436 73/861.355 |
| 2008/0184813 A1* | 8/2008 | Patten | ............... | G01F 1/8413 73/861.355 |
| 2016/0061708 A1 | 3/2016 | Kravitz et al. | | |

OTHER PUBLICATIONS

Agoston A et al: "Evaluation of a vibrating micromachined cantilever sensor for measuring the viscosity of complex organic liquids", Sensors and Actuators A, Elsevier Sequoia S.A., Lausanne, CH, vol. 123-124, Sep. 23, 2005 (Sep. 23, 2005), pp. 82-86, XP027307161, ISSN: 0924-4247 [retrieved on Sep. 23, 2005].
Wilson et al: "Viscosity and density values from excitation level response of piezoelectric-excited cantilever sensors",Sensors and Actuators A, Elsevier Sequoia S.A., Lausanne, CH, vol. 138, No. 1, Jul. 3, 2007 (Jul. 3, 2007), pp. 44-51, XP022138363, ISSN: 0924-4247, DOI: 10.1018/J. SNA.2007.04.050 section 4.

* cited by examiner

DETERMINING A VIBRATION RESPONSE PARAMETER OF A VIBRATORY ELEMENT

TECHNICAL FIELD

The embodiments described below relate to vibratory sensors and, more particularly, to determining a vibration response parameter of a vibratory element in a vibratory sensor.

BACKGROUND

Vibratory sensors, such as vibratory densitometers and vibratory viscometers, operate by detecting motion of a vibrating element that vibrates in the presence of a fluid to be characterized. The vibratory element has a vibration response that may have a vibration response parameter such as a resonant frequency or quality factor Q. The vibration response of the vibrating element is generally affected by the combined mass, stiffness, and damping characteristics of the vibrating element in combination with the fluid. Properties associated with the fluid, such as density, viscosity, temperature and the like, can be determined by processing a vibration signal or signals received from one or more motion transducers associated with the vibrating element. The processing of the vibration signal may include determining the vibration response parameter.

FIG. 1 shows a prior art vibratory sensor comprising a vibratory element and meter electronics coupled to the vibratory element. The prior art vibratory sensor includes a driver for vibrating the vibratory element and a pickoff that creates a vibration signal in response to the vibration. The vibration signal is typically a continuous time or analog signal. The meter electronics receives the vibration signal and processes the vibration signal to generate one or more fluid characteristics or fluid measurements. The meter electronics determines both the frequency and the amplitude of the vibration signal. The frequency and amplitude of the vibration signal can be further processed to determine a density of the fluid.

The prior art vibratory sensor provides a drive signal for the driver using a closed-loop circuit. The drive signal is typically based on the received vibration signal. The prior art closed-loop circuit modifies or incorporates the vibration signal or parameters of the vibration signal into the drive signal. For example, the drive signal may be an amplified, modulated, or an otherwise modified version of the received vibration signal. The received vibration signal can therefore comprise a feedback that enables the closed-loop circuit to achieve a target frequency. Using the feedback, the closed-loop circuit incrementally changes the drive frequency and monitors the vibration signal until the target frequency is reached.

Fluid properties, such as the viscosity and density of the fluid, can be determined from the frequencies where the phase difference between the drive signal and the vibration signal is 135° and 45°. These desired phase differences, denoted as first off-resonant phase difference $\phi_1$ and second off-resonant phase difference $\phi_2$, can correspond to the half power or 3 dB frequencies. The first off-resonant frequency $\omega_1$ is defined as a frequency where the first off-resonant phase difference $\phi_1$ is 135°. The second off-resonant frequency $\omega_2$ is defined as a frequency where the second off-resonant phase difference $\phi_2$ is 45°. Density measurements made at the second off-resonant frequency $\omega_2$ can be independent of fluid viscosity. Accordingly, density measurements made where the second off-resonant phase difference $\phi_2$ is 45° can be more accurate than density measurements made at other phase differences.

The first and second off-resonant phase differences $\phi_1$, $\phi_2$ are typically not known prior to measurement. Accordingly, the closed-loop circuit must incrementally approach the first and second off-resonant phase differences $\phi_1$, $\phi_2$ using the feedback as described in the foregoing. The incremental approach associated with the closed-loop circuit can cause a delay in determining the vibration response parameter and, therefore, cause a delay in determining the viscosity, density, or other properties of the fluid. The delays in determining such measurements can be prohibitively expensive in many applications of the vibratory sensor.

Accordingly, there is a need for determining a vibration response parameter of a vibratory element. There is also a need for determining the vibration response parameter in a desirably fast and accurate manner.

SUMMARY

A method of determining a vibration response parameter of a vibratory element is provided. According to an embodiment, the method comprises vibrating the vibratory element at a first frequency with a first drive signal, receiving a first vibration signal from the vibratory element vibrated at the first frequency, measuring a first phase difference, the first phase difference being a phase difference between the first drive signal and the first vibration signal. The method further comprises vibrating the vibratory element at a second frequency with a second drive signal, receiving a second vibration signal from the vibratory element vibrated at the second frequency, measuring a second phase difference, the second phase difference being a phase difference between the second drive signal and the second vibration signal, and using the first phase difference and the second phase difference to determine at least one of a phase difference, and a frequency of the vibratory element.

A vibratory sensor for determining a vibration response parameter of a vibratory element is provided. According to an embodiment, the vibratory meter comprises a vibratory element configured to be vibrated at a first frequency with a first drive signal, vibrated at a second frequency with a second drive signal. According to the embodiment, the vibratory sensor also comprises a meter electronics communicatively coupled to the vibratory element and configured to receive the first drive signal, receive a first vibration signal from the vibratory element vibrated at the first frequency, and receive a second vibration signal from the vibratory element vibrated at the second frequency. According to the embodiment, the meter electronics is also configured to measure a first phase difference, the first phase difference being a phase difference between the first drive signal and the first vibration signal, measure a second phase difference, the second phase difference being a phase difference between the second drive signal and the second vibration signal, and use the first phase difference and the second phase difference to determine at least one of a phase difference, and a frequency of the vibratory element.

ASPECTS

According to an aspect, a method (900, 1000) of determining a vibration response parameter of a vibratory element (104) comprises vibrating the vibratory element (104) at a first frequency with a first drive signal, receiving a first vibration signal from the vibratory element (104) vibrated at the first frequency, measuring a first phase difference, the first phase difference being a phase difference between the first drive signal and the first vibration signal. The method (900, 1000) also comprises vibrating the vibratory element (104) at a second frequency with a second drive signal, receiving a second vibration signal from the vibratory element (104) vibrated at the second frequency, measuring a second phase difference, the second phase difference being a phase difference between the second drive signal and the second vibration signal. The method (900, 1000) also comprises using the first phase difference and the second phase difference to determine at least one of a phase difference, and a frequency of the vibratory element (104).

Preferably, the determined at least one of the phase difference and the frequency of the vibratory element (104) is a substantially linear approximation calculated from the first phase difference and the second phase difference.

Preferably, the determined at least one frequency of the vibratory element (104) is one of a resonant frequency $\omega 0$, a first off-resonant frequency $\omega 1$, and a second off-resonant frequency $\omega 2$ of the vibratory element (104).

Preferably, the determined at least one phase difference is one of a resonant phase difference $\phi 0$, a first off-resonant phase difference $\phi 1$, and a second off-resonant phase difference $\phi 2$.

Preferably, the method (900, 1000) further comprises using the first phase difference and the second phase difference to calculate a linear approximation of a Q value of the vibratory element (104).

Preferably, the determination of the at least one of the phase difference and the frequency of the vibratory element (104) is determined by one of a linear interpolation and a linear extrapolation.

Preferably, the determined at least one of the phase difference and the frequency of the vibratory element (104) is used to calculate at least one of a viscosity and a density of a fluid measured by the vibratory element (104).

Preferably, the method (900, 1000) further comprises determining if the first measured phase difference and the second measured phase difference is within a linear region of a phase response of a vibratory element (104).

According to an aspect, a vibratory sensor (5) for determining a vibration response parameter of a vibratory element (104) comprises a vibratory element (104) configured to be vibrated at a first frequency with a first drive signal, vibrated at a second frequency with a second drive signal. The vibratory sensor (5) also comprises a meter electronics (20) communicatively coupled to the vibratory element (104) and configured to receive the first drive signal, receive a first vibration signal from the vibratory element (104) vibrated at the first frequency, and receive a second vibration signal from the vibratory element (104) vibrated at the second frequency. The meter electronics (20) is also configured to measure a first phase difference, the first phase difference being a phase difference between the first drive signal and the first vibration signal, measure a second phase difference, the second phase difference being a phase difference between the second drive signal and the second vibration signal, and use the first phase difference and the second phase difference to determine at least one of a phase difference, and a frequency of the vibratory element (104).

Preferably, the determined at least one of the phase difference and the frequency of the vibratory element (104) is a substantially linear approximation calculated from the first phase difference and the second phase difference.

Preferably, the determined at least one frequency of the vibratory element (104) is one of a resonant frequency $\omega 0$, a first off-resonant frequency $\omega 1$, and a second off-resonant frequency $\omega 2$ of the vibratory element (104).

Preferably, the determined at least one phase difference is one of a resonant phase difference $\phi 0$, a first off-resonant phase difference $\phi 1$, and a second off-resonant phase difference $\phi 2$.

Preferably, the meter electronics (20) is further configured to use the first phase difference and the second phase difference to calculate a linear approximation of a Q value of the vibratory element (104).

Preferably, the meter electronics (20) is configured to determine the at least one of the phase difference and the frequency of the vibratory element (104) using one of a linear interpolation and a linear extrapolation.

Preferably, the meter electronics (20) is further configured to calculate at least one of a viscosity and a density of a fluid measured by the vibratory element using the at least one of the phase difference and the frequency of the vibratory element (104).

Preferably, the meter electronics (20) is further configured to determine if the first measured phase difference and the second measured phase difference is within a linear region of a phase response of the vibratory element (104).

BRIEF DESCRIPTION OF THE DRAWINGS

The same reference number represents the same element on all drawings. It should be understood that the drawings are not necessarily to scale.

DETAILED DESCRIPTION

FIGS. 2-10 and the following description depict specific examples to teach those skilled in the art how to make and use the best mode of embodiments of determining a vibration response parameter of a vibratory element. For the purpose of teaching inventive principles, some conventional aspects have been simplified or omitted. Those skilled in the art will appreciate variations from these examples that fall within the scope of the present description. Those skilled in the art will appreciate that the features described below can be combined in various ways to form multiple variations of determining the vibration response parameter of the vibratory element. As a result, the embodiments described below are not limited to the specific examples described below, but only by the claims and their equivalents.

Figure 1:
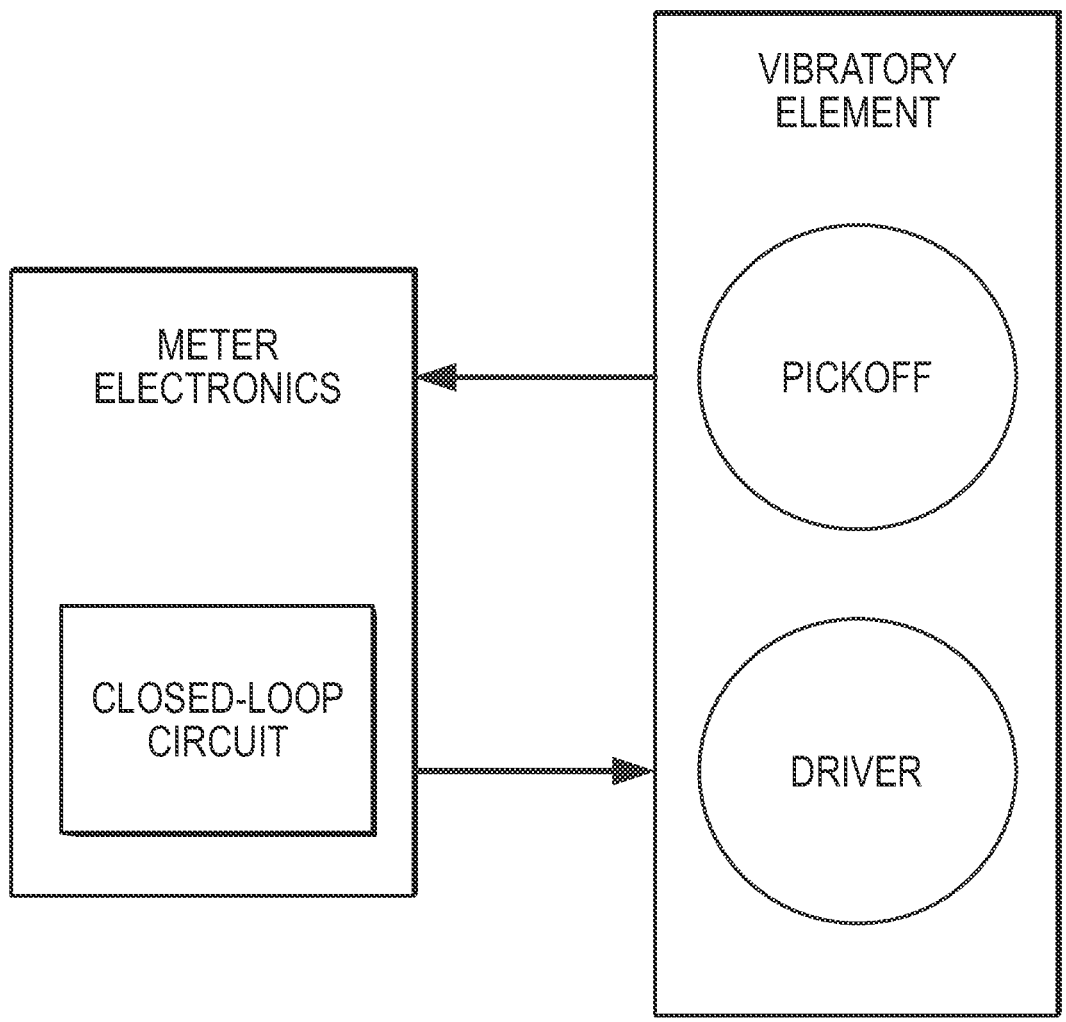
FIG. 1 shows a prior art vibratory sensor comprising a vibratory element and meter electronics coupled to the vibratory element.
Figure 2:
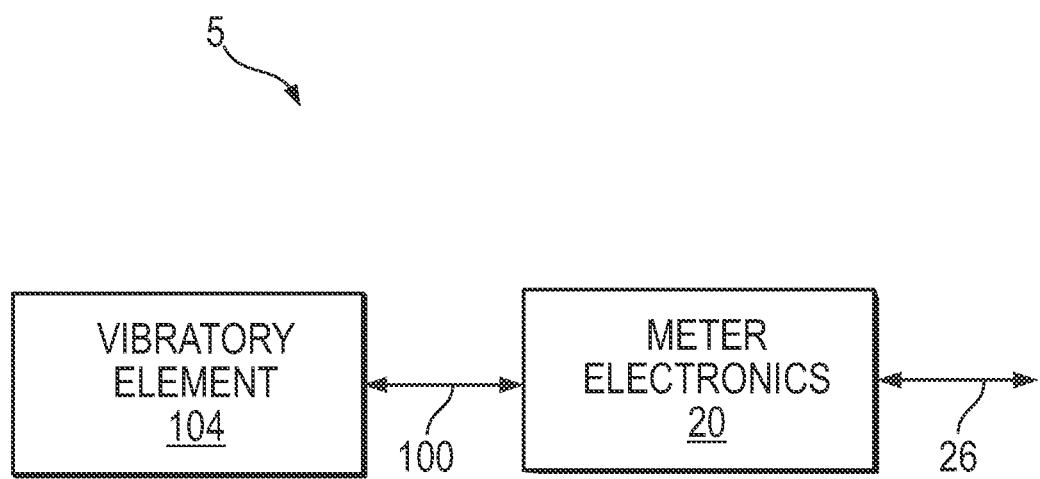
FIG. 2 shows a vibratory sensor 5 according to an embodiment.

FIG. 2 shows a vibratory sensor 5 according to an embodiment. The vibratory sensor 5 may comprise a vibratory element 104 and meter electronics 20, wherein the vibratory element 104 is coupled to the meter electronics 20 by a lead or leads 100. In some embodiments, the vibratory sensor 5 may comprise a vibratory tine sensor or fork density sensor (see FIG. 3 and the accompanying discussion). However, other vibratory sensors are contemplated and are within the scope of the description and claims.

The vibratory sensor 5 may be at least partially immersed into a fluid to be characterized. The fluid can comprise a liquid or a gas. Alternatively, the fluid can comprise a multi-phase fluid, such as a liquid that includes entrained gas, entrained solids, multiple liquids, or combinations thereof. Some exemplary fluids include cement slurries, petroleum products, or the like. The vibratory sensor 5 may be mounted in a pipe or conduit, a tank, a container, or other fluid vessels. The vibratory sensor 5 can also be mounted in a manifold or similar structure for directing a fluid flow. However, other mounting arrangements are contemplated and are within the scope of the description and claims.

The vibratory sensor 5 operates to provide fluid measurements. The vibratory sensor 5 may provide fluid measurements including one or more of a fluid density and a fluid viscosity for a fluid, including flowing or non-flowing fluids. The vibratory sensor 5 may provide fluid measurements including a fluid mass flow rate, a fluid volume flow rate, and/or a fluid temperature. This listing is not exhaustive and the vibratory sensor 5 may measure or determine other fluid characteristics.

The meter electronics 20 can provide electrical power to the vibratory element 104 via the lead or leads 100. The meter electronics 20 controls operation of the vibratory element 104 via the lead or leads 100. For example, the meter electronics 20 may generate a drive signal and provide the generated drive signal to the vibratory element 104, wherein the vibratory element 104 generates a vibration in one or more vibratory components using the generated drive signal. The generated drive signal can control the vibrational amplitude and frequency of the vibratory element 104. The generated drive signal can also control the vibrational duration and/or vibrational timing.

The meter electronics 20 can also receive a vibration signal or signals from the vibratory element 104 via the lead or leads 100. The meter electronics 20 may process the vibration signal or signals to generate a density measurement, for example. The meter electronics 20 processes the vibration signal or signals received from the vibratory element 104 to determine a frequency of the signal or signals. Further, or in addition, the meter electronics 20 processes the vibration signal or signals to determine other characteristics of the fluid, such as a viscosity or a phase difference between signals, that can be processed to determine a fluid flow rate, for example. As can be appreciated, the phase difference is typically measured or expressed in spatial units such as degrees or radians although any suitable unit can be employed such as time-based units. If time-based units are employed, then the phase difference may be referred to by those in the art as a time delay between the vibration signal and the drive signal. Other vibrational response characteristics and/or fluid measurements are contemplated and are within the scope of the description and claims.

The meter electronics 20 can be further coupled to a communication link 26. The meter electronics 20 may communicate the vibration signal over the communication link 26. The meter electronics 20 may also process the received vibration signal to generate a measurement value or values and may communicate the measurement value or values over the communication link 26. In addition, the meter electronics 20 can receive information over the communication link 26. For example, the meter electronics 20 may receive commands, updates, operational values or operational value changes, and/or programming updates or changes over the communication link 26.

Figure 3:
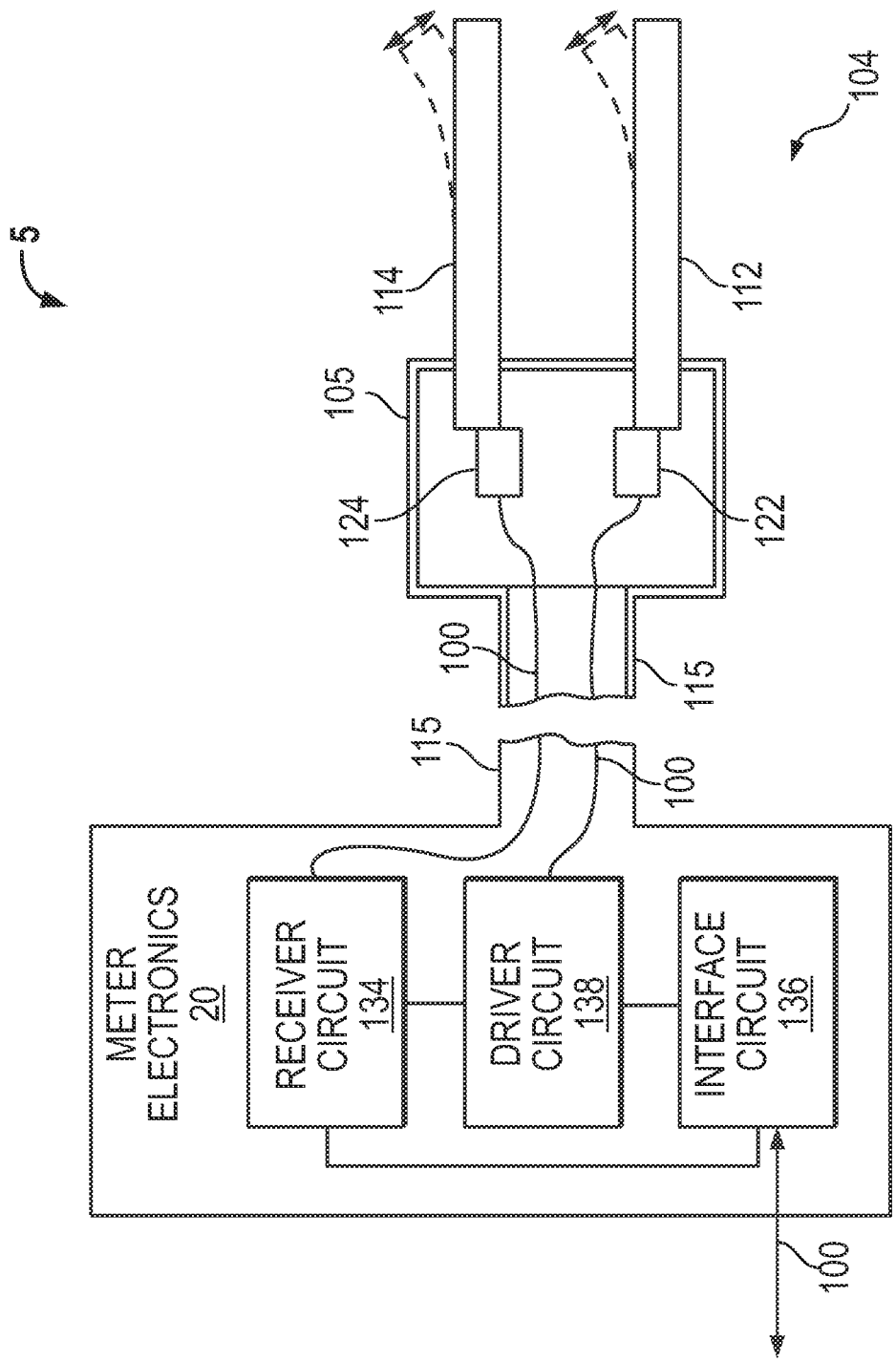
FIG. 3 shows the vibratory sensor 5 according to an embodiment.

FIG. 3 shows the vibratory sensor 5 according to an embodiment. The meter electronics 20 is coupled to the vibratory element 104 by a shaft 115 in the embodiment shown. The shaft 115 may be of any desired length. The shaft 115 may be at least partially hollow. Wires or other conductors may extend between the meter electronics 20 and the vibratory element 104 through the shaft 115. The meter electronics 20 includes circuit components such as a receiver circuit 134, an interface circuit 136, and a driver circuit 138. In the embodiment shown, the receiver circuit 134 and the driver circuit 138 are directly coupled to the leads of the vibratory element 104. Alternatively, the meter electronics 20 can comprise a separate component or device from the vibratory element 104, wherein the receiver circuit 134 and the driver circuit 138 are coupled to the vibratory element 104 via the lead or leads 100.

In the embodiment shown, the vibratory element 104 of the vibratory sensor 5 comprises a tuning fork structure, wherein the vibratory element 104 is at least partially immersed in the fluid being measured. The vibratory element 104 includes a housing 105 that can be affixed to another structure, such as a pipe, conduit, tank, receptacle, manifold, or any other fluid-handling structure. The housing 105 retains the vibratory element 104 while the vibratory element 104 remains at least partially exposed. The vibratory element 104 is therefore configured to be immersed in the fluid.

The vibratory element 104 in the embodiment shown includes first and second tines 112 and 114 that are configured to extend at least partially into the fluid. The first and second tines 112 and 114 comprise elongated elements that may have any desired cross-sectional shape. The first and second tines 112 and 114 may be at least partially flexible or resilient in nature. The vibratory sensor 5 further includes corresponding first and second piezo elements 122 and 124 that comprise piezo-electric crystal elements. The first and second piezo elements 122 and 124 are located adjacent to the first and second tines 112 and 114, respectively. The first and second piezo elements 122 and 124 are configured to contact and mechanically interact with the first and second tines 112 and 114.

The first piezo element 122 is in contact with at least a portion of the first tine 112. The first piezo element 122 is also electrically coupled to the driver circuit 138. The driver circuit 138 provides the generated drive signal to the first piezo element 122. The first piezo element 122 expands and contracts when subjected to the generated drive signal. As a result, the first piezo element 122 may alternatingly deform and displace the first tine 112 from side to side in a vibratory motion (see dashed lines), disturbing the fluid in a periodic, reciprocating manner.

The second piezo element 124 is shown as coupled to a receiver circuit 134 that produces the vibration signal corresponding to the deformations of the second tine 114 in the fluid. Movement of the second tine 114 causes a corresponding electrical vibration signal to be generated by the second piezo element 124. The second piezo element 124 transmits the vibration signal to the meter electronics 20. The meter electronics 20 includes the interface circuit 136. The interface circuit 136 can be configured to communicate with external devices. The interface circuit 136 communicates a vibration measurement signal or signals and may communicate determined fluid characteristics to one or more external devices. The meter electronics 20 can transmit vibration signal characteristics via the interface circuit 136, such as a vibration signal frequency and a vibration signal amplitude of the vibration signal. The meter electronics 20 may transmit fluid measurements via the interface circuit 136, such as a density and/or viscosity of the fluid, among other things. Other fluid measurements are contemplated and are within the scope of the description and claims. In addition, the interface circuit 136 may receive communications from external devices, including commands and data for generating measurement values, for example. In some embodiments, the receiver circuit 134 is coupled to the driver circuit 138, with the receiver circuit 134 providing the vibration signal to the driver circuit 138.

The driver circuit 138 generates the drive signal for the vibratory element 104. The driver circuit 138 can modify characteristics of the generated drive signal. The driver circuit 138 includes an open-loop drive. The open-loop drive may be used by the driver circuit 138 to generate the drive signal and supply the generated drive signal to the vibratory element 104 (e.g., to the first piezo element 122). In some embodiments, the open-loop drive generates the drive signal to achieve a target phase difference $\phi_t$, commencing at an initial frequency $\omega_i$. The open-loop drive may not operate based on feedback from the vibration signal, as will be described in more detail in the following with reference to FIG. 4.

Figure 4:
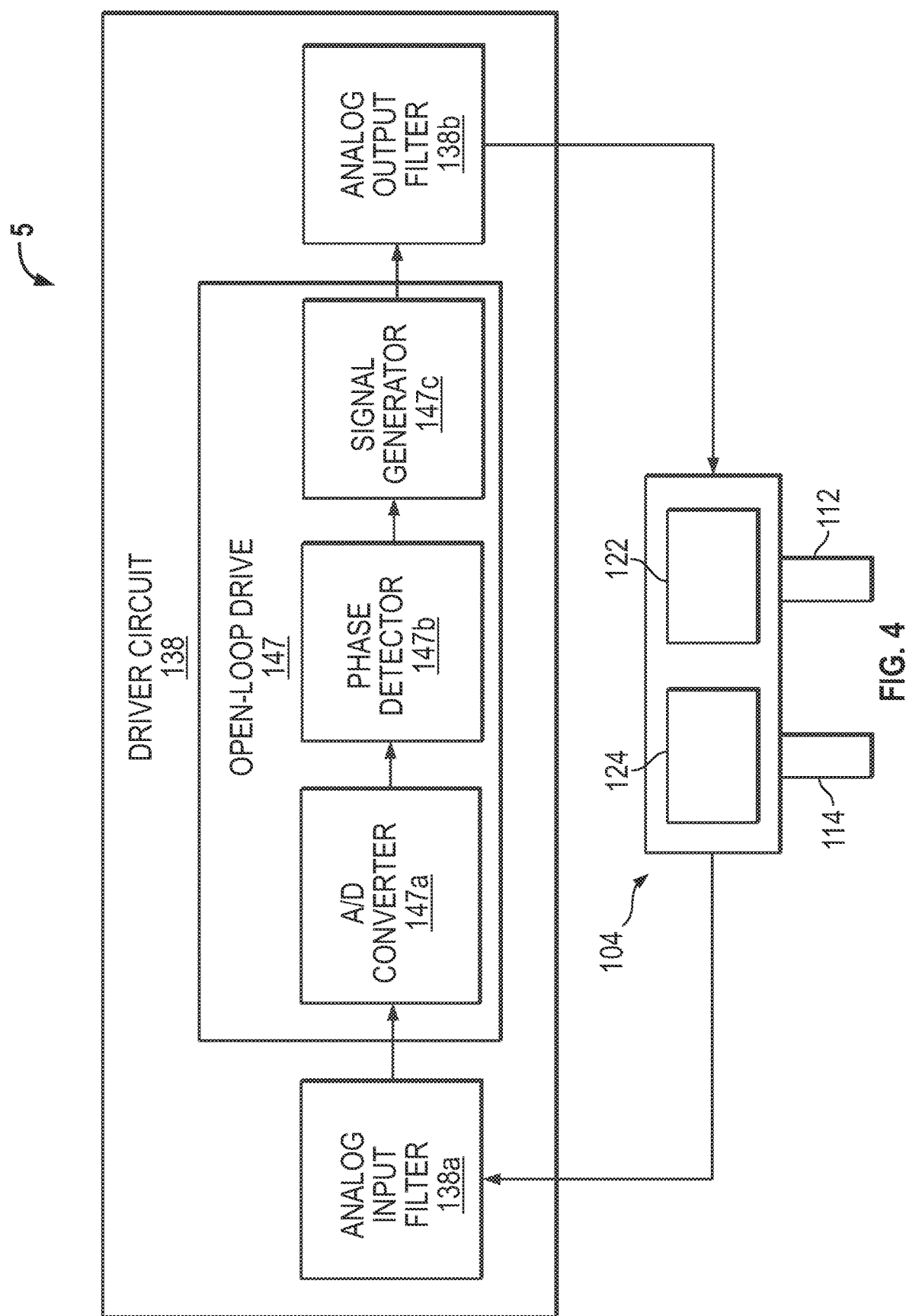
FIG. 4 shows a block diagram of the vibratory sensor 5 with a more detailed representation of the driver circuit 138.

FIG. 4 shows a block diagram of the vibratory sensor 5 with a more detailed representation of the driver circuit 138. The vibratory sensor 5 is shown with the driver circuit 138. The receiver circuit 134 and the interface circuit 136 are not shown for clarity. The driver circuit 138 includes an analog input filter 138a and an analog output filter 138b that are coupled to the open-loop drive 147. The analog input filter 138a filters the vibration signal and the analog output filter 138b filters the generated drive signal.

The open-loop drive 147 includes an analog to digital converter 147a that is coupled to a phase detector 147b. The phase detector 147b is coupled to a signal generator 147c. Also shown is the vibratory element 104, which includes the first piezo element 122 and the second piezo element 124. The open-loop drive 147 can be implemented with a digital signal processor that is configured to execute one or more codes or programs that sample, process, and generate signals. Additionally or alternatively, the open-loop drive 147 can be implemented with an electronics circuit coupled to the digital signal processor or the like.

The vibration signal provided by the first piezo element 122 is sent to the analog input filter 138a. The analog input filter 138a filters the vibration signal prior to the vibration signal being sampled by the analog to digital converter 147a. In the embodiment shown, the analog input filter 138a can be comprised of a low pass filter with cutoff frequency that is about half the sample rate of the open-loop drive 147 although any suitable low pass filter can be employed. The low pass filter can be provided by passive components such as an inductor, a capacitor, and a resistor although any suitable components, distributed or discrete, such as an operational amplifier filter, can be employed.

The analog to digital converter 147a can sample the filtered vibration signal to form a sampled vibration signal. The analog to digital converter 147a can also sample the generated drive signal through a second channel (not shown). The sampling can be by any appropriate sampling method. As can be appreciated, the generated drive signal sampled by the analog to digital converter 147a does not have noise associated with the vibration signal. The generated drive signal is provided to the phase detector 147b.

The phase detector 147b can compare the phases of the sampled vibration and generated drive signal. The phase detector 147b can be a processor configured to execute one or more codes or programs that sample, process, and generate signals to detect a phase difference between two signals, as will be described in more detail in the following with reference to FIG. 5. Still referring to the embodiment of FIG. 4, the comparison provides a measured phase difference $\phi_m$ between the sampled vibration signal and the sampled generated drive signal.

The measured phase difference $\phi_m$ is compared with the target phase difference $\phi_t$. The target phase difference $\phi_t$ is a desired phase difference between the vibration signal and the generated drive signal. For example, in an embodiment where the target phase difference $\phi_t$ is approximately 45°, the difference between the measured phase difference $\phi_m$ and the target phase difference $\phi_t$ can be zero if the measured phase difference $\phi_m$ is also the same as or about 45°. However, any appropriate target phase difference $\phi_t$ can be employed in alternative embodiments. Using the comparison between the measured phase difference $\phi_m$ and the target phase difference $\phi_t$, the phase detector 147b can generate a command frequency $\omega_c$.

The command frequency $\omega_c$ can be employed to generate the drive signal. Additionally or alternatively, an initial frequency that is not determined from the comparison between the measured phase difference $\phi_m$ and the target phase difference $\phi_t$ can be employed. The initial frequency $\omega_i$ could be a preselected frequency used to form an initial generated drive signal. The initial generated drive signal can be sampled as described in the foregoing and compared with the sampled vibration signal. The comparison between the sampled initial generated drive signal and the sampled vibration signal can be used to generate the command frequency $\phi_c$. The command frequency $\omega_c$ and the initial frequency $\omega_i$ can have units of radians per second although any suitable units such as, for example, Hertz (Hz) can be employed. The command frequency $\omega_c$ or the initial frequency $\omega_i$ can be provided to the signal generator 147c.

The signal generator 147c can receive the command frequency $\omega_c$ from the phase detector 147b and provide the generated drive signal with a frequency that is the same as the command frequency $\omega_c$. The generated drive signal may be sent, as discussed in the foregoing, to the analog to digital converter 147a. The generated drive signal is also sent to the first piezo element 122 via the analog output filter 138b. Additionally or alternatively, the generated drive signal can be sent to other components in other embodiments.

As discussed in the foregoing, the vibratory element 104 has a vibration response due to the drive signal. The vibration response has vibration response parameters, such as a resonant frequency $\omega 0$, quality factor Q, or the like, which can be employed to calculate various properties of the fluid being measured. The vibration response and exemplary vibration response parameters, as well as how the vibration response parameters can be used to calculate the properties of the fluid are discussed in more detail in the following.

Figure 5:
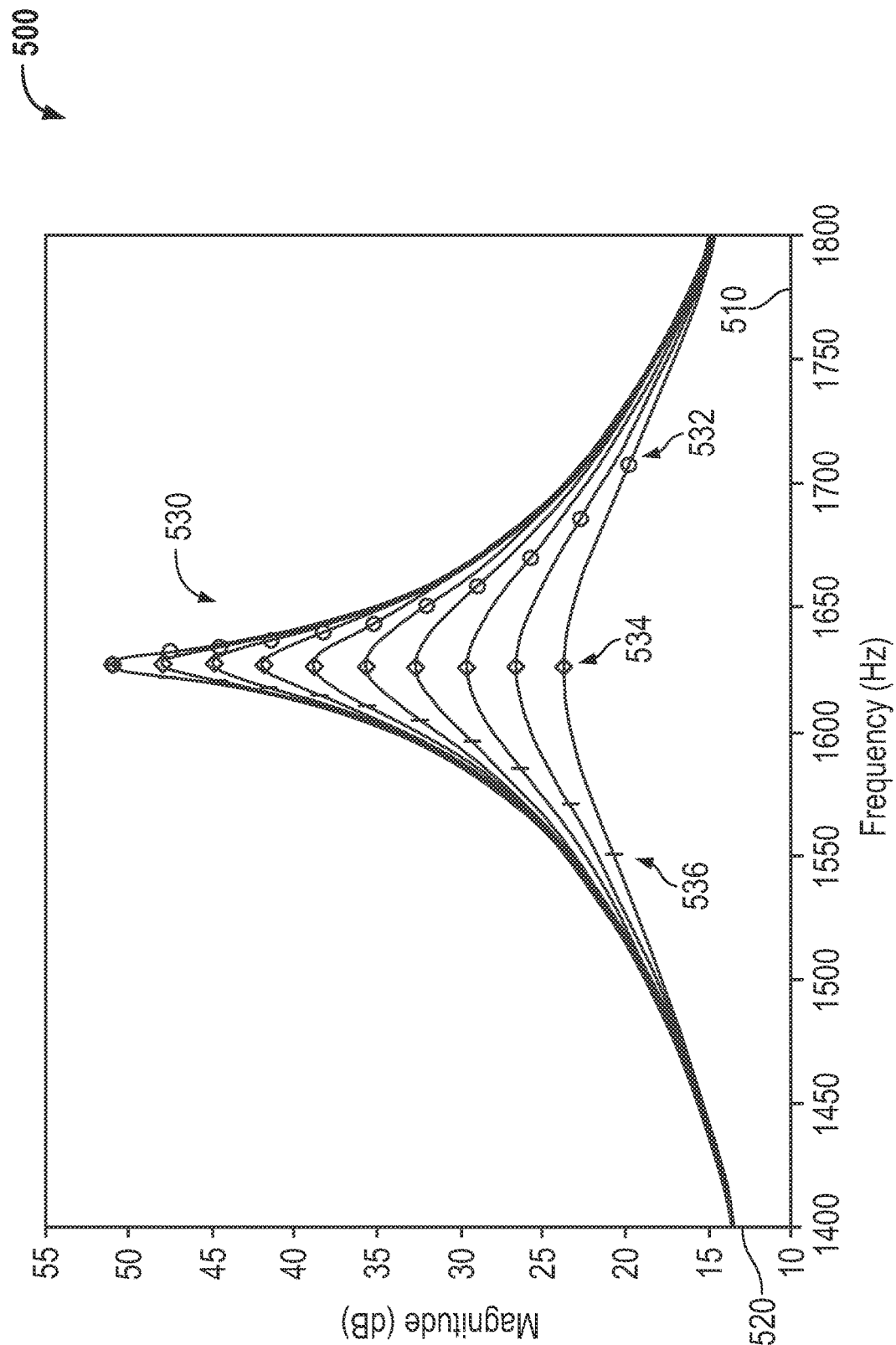
FIG. 5 shows a frequency response graph 500 illustrating a vibration response of a vibratory element.

FIG. 5 shows a frequency response graph 500 illustrating a vibration response of a vibratory element. The vibratory element may be the exemplary vibratory element 104 described in the foregoing with reference to FIGS. 2-4. The frequency response graph 500 includes a frequency axis 510 and a magnitude axis 520. The frequency axis 510 is shown in units of Hz although any suitable frequency unit may be employed, such as, for example, radians per second. The magnitude axis 520 is shown with a decibel (dB) scale. The magnitude axis 520 can be determined from any appropriate unit, such as, for example, volts or amps.

The frequency response graph 500 also includes frequency response plots 530. The frequency response plots 530 may represent the vibration responses of the vibratory element 104 described in the foregoing, although any suitable vibratory element may be employed in alternative embodiments. As shown in FIG. 5, the frequency response plots 530 are comprised of individual frequency response plots for fluids with different vibration damping properties. For example, the plot with the lowest magnitude at the resonant frequency may be the flattest due to the vibratory element 104 being immersed in a viscous and dense fluid. The plot with the largest magnitude at the resonant frequency may be the least flat due to the vibratory element being immersed in a fluid with low viscosity relative to the fluids associated with the other plots in the frequency response plots 530. As can be appreciated, each of the frequency response plots 530 has different associated vibration response parameters.

For example, in the embodiment shown in FIG. 5, each of the frequency response plots 530 has three markers which indicate a first off-resonant frequency ω1, a second off-resonant frequency ω2, and a resonant frequency ω0, which are vibration response parameters of a vibration response. The first off-resonant frequency ω1 is indicated by a circle marker 532. The second off-resonant frequency ω1 is indicated by a vertical tic marker 536. The resonant frequency ω0 is indicated by a diamond marker 534. As can be appreciated by referring to the diamond markers 534, the resonant frequency ω0 is substantially the same for each of the frequency response plots 530.

In some embodiments, the resonant frequency ω0 may be determined from the first off-resonant frequency ω1 and the second off-resonant frequency ω2. For example, the resonant frequency ω0 can be determined from an average of the first off-resonant frequency ω1 and the second off-resonant frequency ω2:

$$\omega 0 = \frac{(\omega 1 + \omega 2)}{2}. \quad (1)$$

However, in alternative embodiments, the resonant frequency φ0 can be determined in other ways, such as measuring the frequency at peak magnitude while sweeping a range of frequencies.

The quality factor Q can be determined from the first off-resonant frequency ω1, the second off-resonant frequency ω2, and the resonant frequency ω0. For example, the quality factor Q can be determined from:

$$Q = \frac{\omega 0}{(\omega 1 - \omega 2)}. \quad (2)$$

As can be appreciated, the quality factor Q is different for each curve. The quality factor Q may be different for each of the frequency response plots 530 due to various reasons, such as, for example, the fluid associated with each of the frequency response plots 530 having different viscosity or density.

The foregoing illustrates how the vibration response parameter can be determined when the first off-resonant frequency ω1 and the second off-resonant frequency ω2 are measured. However, as the following will illustrate, the vibration response parameter can also be determined by measuring a phase difference between a drive signal and a vibration signal. Additionally, the vibration response parameter can also be determined by using frequencies that are not the first or second off-resonant frequency ω1, ω2.

Figure 6:
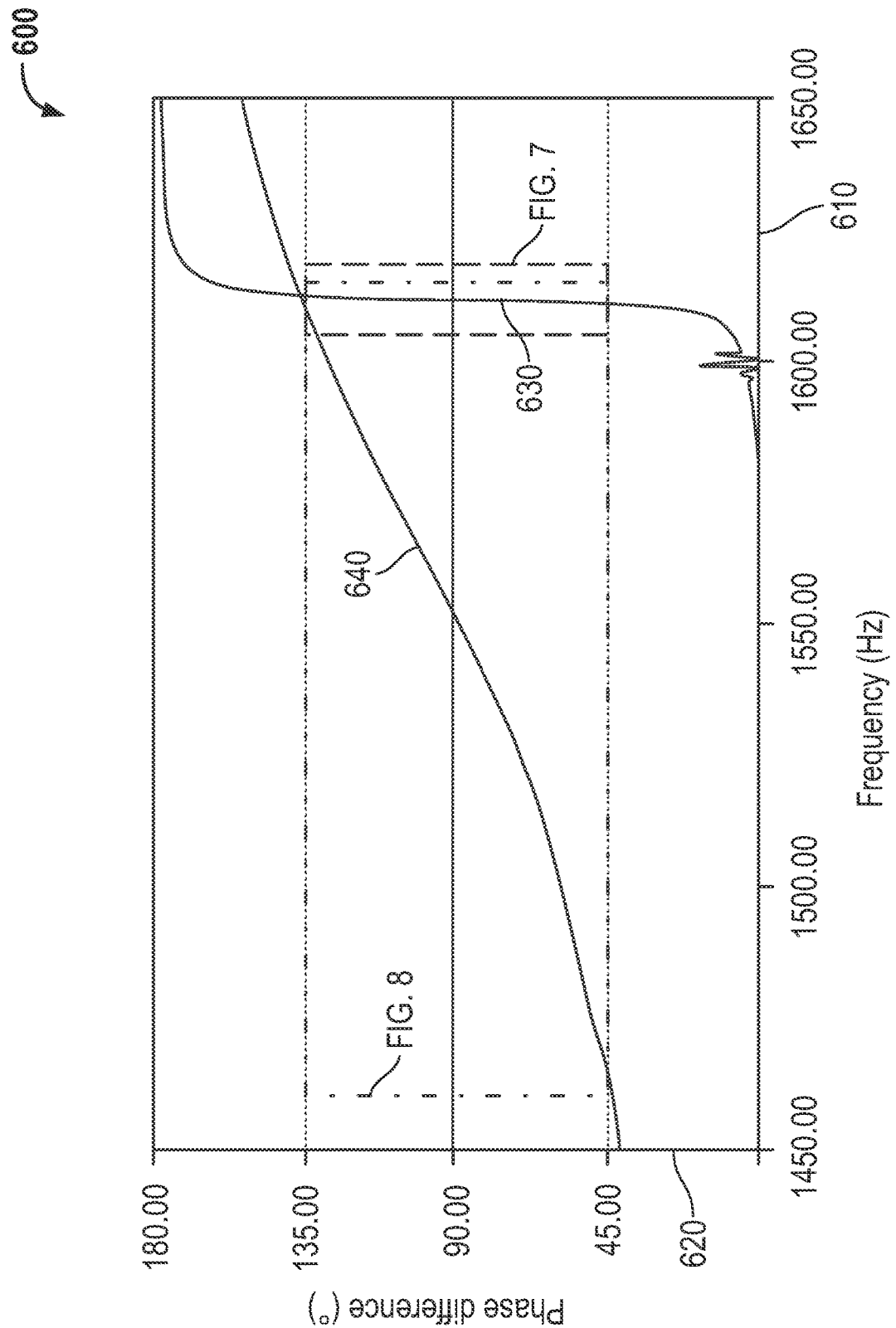
FIG. 6 shows a phase response graph 600 illustrating a vibration response of a vibratory element.

FIG. 6 shows a phase response graph 600 illustrating a vibration response of a vibratory element. The vibratory element may be the vibratory element described in the foregoing with reference to FIGS. 2-4. The phase response graph 600 includes a frequency axis 610, which is an abscissa of the phase response graph 600. The phase response graph 600 also includes a phase difference axis 620, which is an ordinate of the phase response graph 600. The phase response graph 600 also includes a low viscosity phase response plot 630 and a high viscosity phase response plot 640.

As can be appreciated, a substantial portion of the low and high viscosity phase response plots 630, 640 are linear. For example, the low viscosity phase response plot 630 is nearly vertical with a substantially constant slope from about 1610 Hz to about 1613 Hz. In the high viscosity phase response plot 640, between the vibration response frequencies of about 1455 Hz and 1610 Hz, the value of the phase difference increases with a relatively constant slope. As can also be appreciated, the linear portions of the low and high viscosity phase response plots 630, 640 extend between the first off-resonant frequency ω1 (shown as being about 1612.55 Hz at 135° phase difference) and the second off-resonant frequency ω2 (shown as being about 1610.65 at 45° phase difference). The linearity in the low and high viscosity phase response plots 630, 640 can be utilized to determine a frequency or a phase difference between the first off-resonant frequency ω1 and the second off-resonant frequency ω2, as will be explained in more detail in the following with reference to FIGS. 7 and 8.

Figure 7:
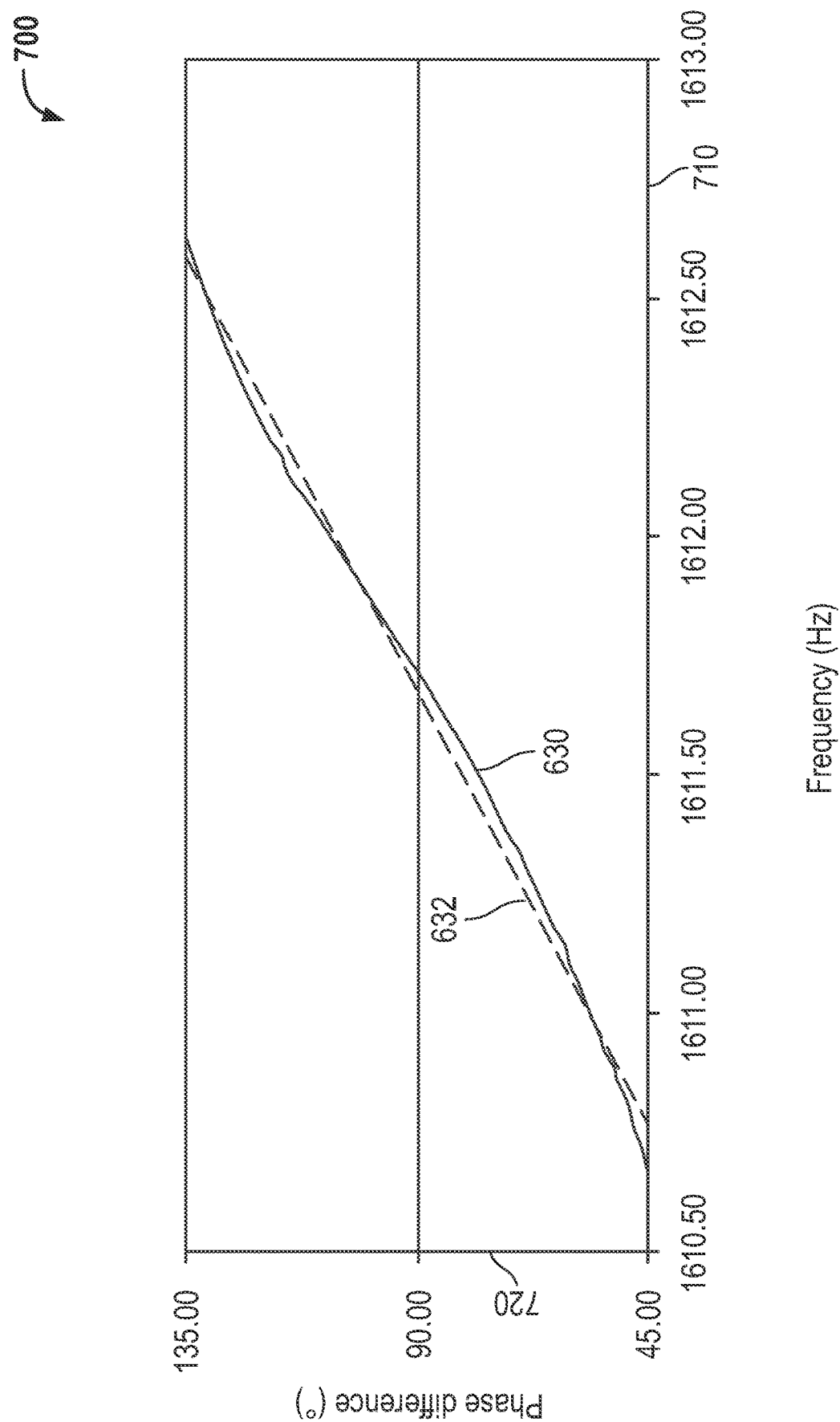
FIG. 7 shows a low viscosity phase response graph 700, which is an enlarged view of the phase response graph 600 shown in FIG. 6.

FIG. 7 shows a low viscosity phase response graph 700, which is an enlarged view of the phase response graph 600 shown in FIG. 6. Due to being enlarged, the low viscosity phase response graph 700 includes a frequency axis 710 that ranges from 1610.50 to 1613.00. Also due to being enlarged, the low viscosity phase response graph 700 includes a phase difference axis 720 that ranges from 45.00 degrees to 135.00 degrees. The low viscosity phase response graph 700 also includes the substantially linear portion of the low viscosity phase response plot 630 described in the foregoing. Also shown in FIG. 7 is an exemplary low viscosity linearization 632 of the low viscosity phase response plot 630.

The low viscosity linearization 632 is relatively close to the low viscosity phase response plot 630. For example, at least two points on the low viscosity linearization 632 are shared with the low viscosity phase response plot 630. The low viscosity linearization 632 is also relatively close to the low viscosity phase response plot 630 along the entire length of the low viscosity phase response plot 630. To illustrate that phase response plots of fluids with differing viscosities can be linearized, we now turn to an enlarged view of the high viscosity phase response plot 640.

Figure 8:
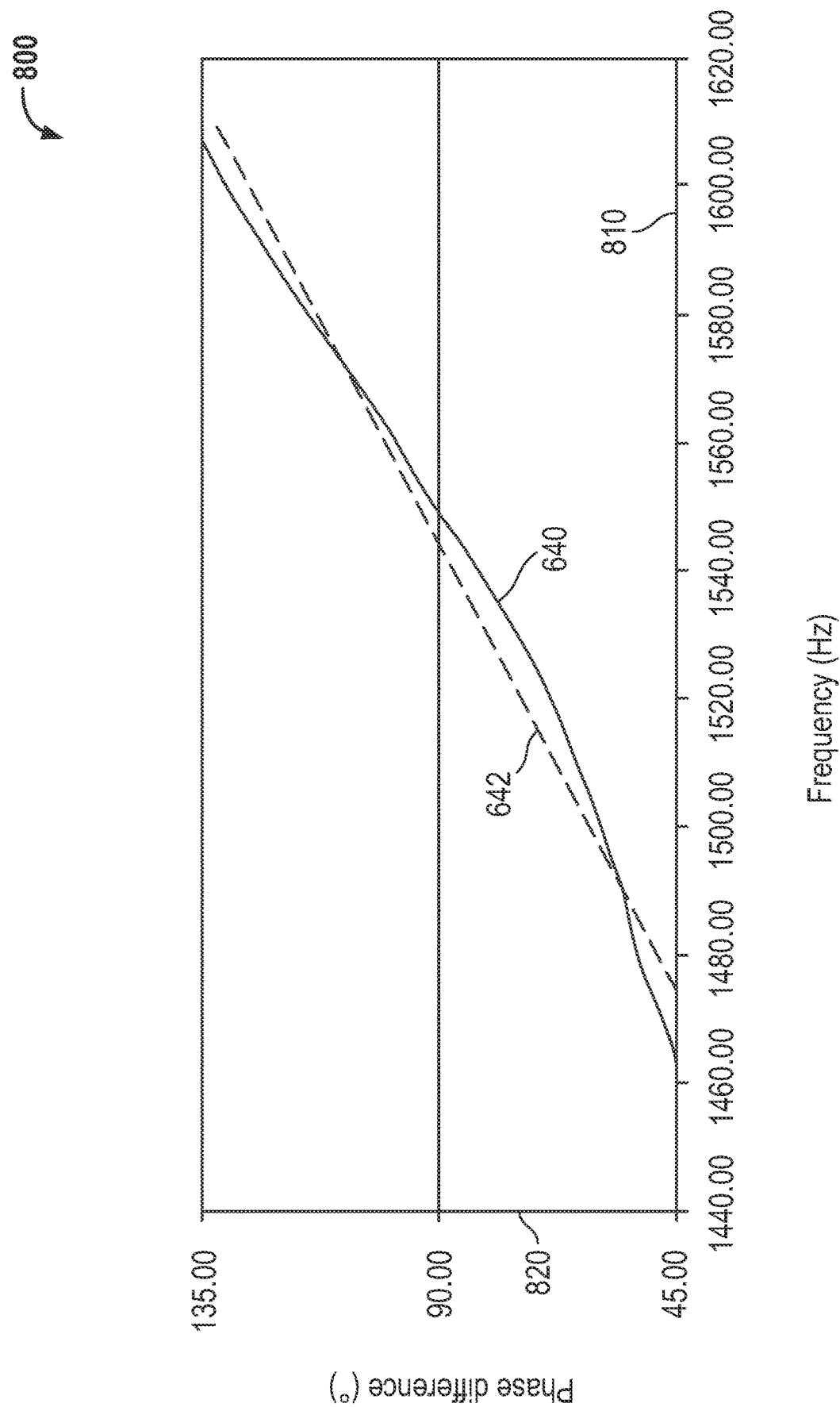
FIG. 8 shows a high viscosity phase response graph 800, which is an enlarged view of the phase response graph 600 shown in FIG. 6.

FIG. 8 shows a high viscosity phase response graph 800, which is an enlarged view of the phase response graph 600 shown in FIG. 6. Due to being enlarged, the high viscosity phase response graph 800 includes a frequency axis 810 that ranges from 1440.00 to 1620.00. Also due to being enlarged, the high viscosity phase response graph 800 includes a phase difference axis 820 that ranges from 45.00 degrees to 135.00 degrees. The high viscosity phase response graph 800 also includes the substantially linear portion of the high viscosity phase response plot 640 described in the foregoing. Also shown in FIG. 8 is an exemplary high viscosity linearization 642 of the high viscosity phase response plot 640.

The high viscosity linearization 642 is relatively close to the high viscosity phase response plot 640. For example, at least two points on the high viscosity linearization 642 are shared with the high viscosity phase response plot 640. The high viscosity linearization 642 is also relatively close to the high viscosity phase response plot 640 along the entire length of the high viscosity phase response plot 640.

In embodiments where linearization is employed to determine a vibration response parameter of the vibratory element, two or more points on each of the phase response plots 630, 640 can be employed to determine a frequency or a phase difference. For example, the linearizations 632, 642 described in the foregoing can be used to calculate the first off-resonant frequency $\omega 1$ and the second off-resonant frequency $\omega 2$. Similarly, the linearizations 632, 642 can be used to calculate the first off-resonant phase difference $\phi 1$ and the second off-resonant phase difference $\phi 2$. Exemplary methods of using the off-resonant frequencies and phase differences $\omega 1$, $\omega 2$, $\phi 1$, $\phi 2$ to determine the vibratory response are described in more detail in the following with reference to FIGS. 9 and 10.

Figure 9:
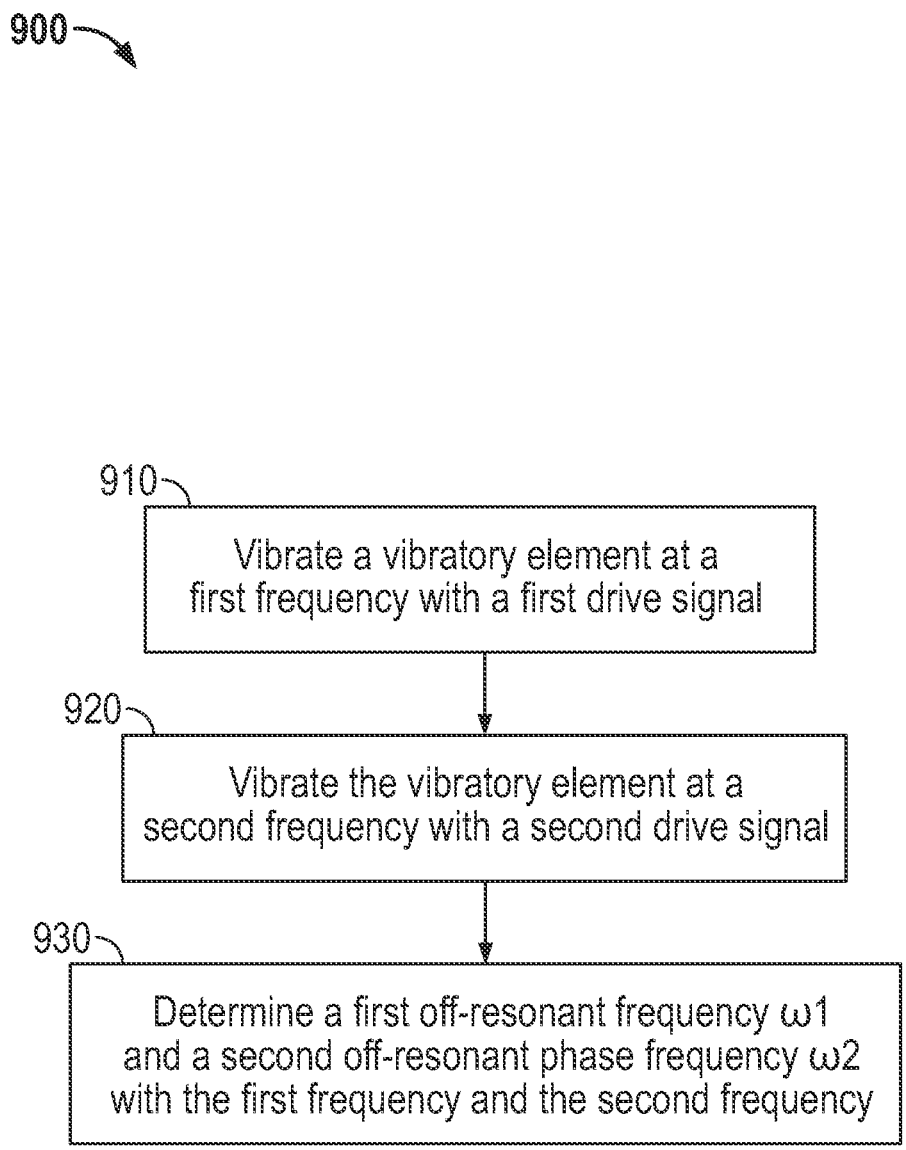
FIG. 9 shows a method 900 of determining a vibration response parameter according to an embodiment.

FIG. 9 shows a method 900 of determining a vibration response parameter according to an embodiment. The method 900 begins by vibrating a vibratory element at a first frequency with a first drive signal in step 910. The vibratory element may be the vibratory element 104 described in the foregoing with reference to FIG. 2-4. In step 920, the method 900 vibrates the vibratory element at a second frequency with a second drive signal. The second drive signal may be different than the first drive signal. Additionally or alternatively, the vibratory element may be vibrated by the first drive signal and the second drive signal at the same or different times. For example, a complex drive signal that is comprised of the first and second drive signal may be applied to the vibratory element to generate the first and second frequency.

In step 930, the method 900 determines the first off-resonant frequency $\omega 1$ and the second off-resonant frequency $\omega 2$ with the first frequency and the second frequency. For example, the meter electronics 20 described in the foregoing may measure the first frequency along with a first phase difference. The meter electronics 20 may also measure a second frequency along with a second phase difference. The meter electronics 20 can determine if the first frequency and corresponding first phase difference and the second frequency and the corresponding second phase difference are within a linear region of a phase response of the vibratory element 104. With reference to the exemplary phase response plots 630, 640 described in the foregoing, the meter electronics 20 may determine if the first and second phase differences are greater than 45 degrees and less than 135 degrees. The method 900 may then calculate a linear approximation of the first off-resonant frequency $\omega 1$ and the second off-resonant frequency $\omega 2$. Additionally or alternatively, the first and second off-resonant phase differences $\phi 1$, $\phi 2$ can also be calculated, as will be explained in more detail in the following.

Figure 10:
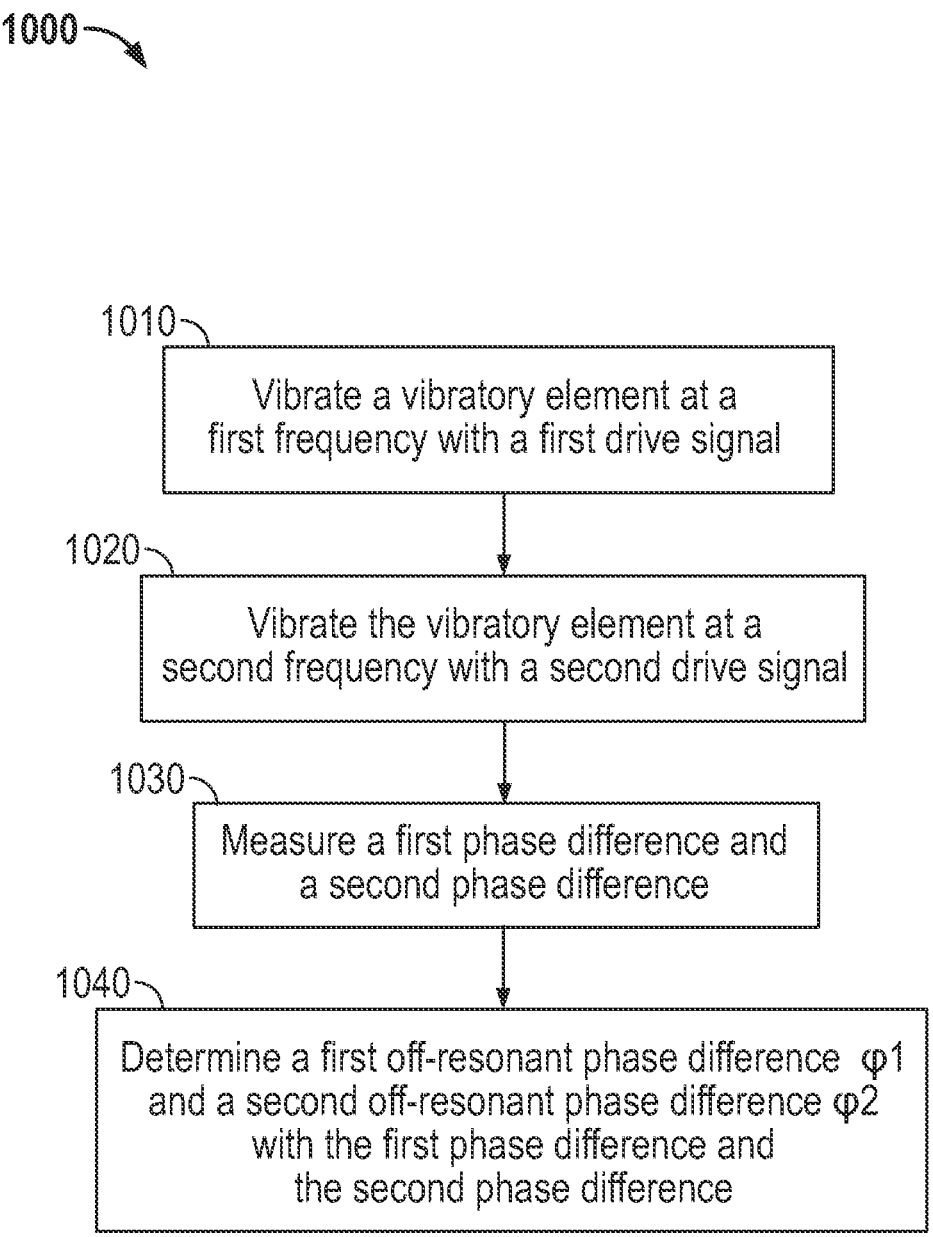
FIG. 10 shows a method 1000 of determining a vibration response parameter according to an embodiment.

FIG. 10 shows a method 1000 of determining a vibration response parameter according to an embodiment. The method 1000 begins by vibrating a vibratory element at a first frequency with a first drive signal in step 1010. The vibratory element may be the vibratory element 104 described in the foregoing with reference to FIGS. 2-4. In step 1020, the method 1000 vibrates the vibratory element at a second frequency with a second drive signal. The second drive signal may be different than the first drive signal. Additionally or alternatively, the vibratory element may be vibrated at the first drive frequency and the second drive frequency at the same or different times. For example, a drive signal may be comprised of the first and second drive signal and applied to the vibratory element to generate a first and second vibration signal.

In step 1030, the method 1000 measures a first phase difference and a second phase difference. For example, the first phase difference may be a phase difference between the first vibration signal and the first drive signal. Similarly, the second phase difference may be a phase difference between the second vibration signal and the second drive signal.

In step 1040, the method 1000 may determine a first off-resonant phase difference $\phi 1$ and a second off-resonant phase difference $\phi 2$ with the first phase difference and the second phase difference. For example, the meter electronics 20 described in the foregoing may measure the first phase difference along with a first frequency. The meter electronics 20 can also measure the second phase difference along with a second frequency. The meter electronics 20 can determine if the first frequency and corresponding first phase difference and the second frequency and the corresponding second phase difference are within a linear region of a phase response of the vibratory element 104. With reference to the exemplary phase response plots 630, 640 described in the foregoing with reference to FIGS. 6-8, the meter electronics 20 may determine if the first and second phase differences are greater than 45 degrees and less than 135 degrees. The method 900 may then calculate a linear approximation of the first off-resonant frequency $\omega 1$ and the second off-resonant frequency $\omega 2$.

The foregoing describes calculating linear approximations of a frequency or a phase difference, which may be the first and second off-resonant frequencies and phase differences $\omega 1$, $\omega 2$, $\phi 1$, $\phi 2$. The linear approximations of the first and second off-resonant frequencies and phase differences $\omega 1$, $\omega 2$, $\phi 1$, $\phi 2$ can be calculated with various methods. For example, the meter electronics 20 described in the foregoing may measure the first and second frequencies and phase differences. The meter electronics 20 can determine if the first frequency and corresponding first phase difference and the second frequency and the corresponding second phase difference are within a linear region of a phase response of the vibratory element 104. For example, with reference to the exemplary phase response plots 630, 640 described in the foregoing, the meter electronics 20 may determine if the first and second phase differences are greater than 45 degrees and less than 135 degrees. The methods 900, 1000 may then calculate a linear approximation of the first off-resonant frequency and phase difference $\omega 1$, $\phi 1$ and the second off-resonant frequency and phase difference $\omega 2$, $\phi 2$.

The linear approximation may be calculated by using extrapolation or interpolation. For example, with reference to the linearizations 632, 642 described in the foregoing, the first and second frequencies and phase differences, the methods 900, 1000 may assume that the first and second frequencies and phase differences are two points along the linearizations 632, 642. Accordingly, the methods 900, 1000 can extrapolate or interpolate the first and second frequencies and phase differences to the first and second off-resonant phase differences $\phi1$, $\phi2$ and the corresponding first and second off-resonant frequencies $\omega1$, $\omega2$. Although the foregoing describes embodiments where the phase differences are greater than 45 degrees and less than 135 degrees, the measured phase differences may be less than 45 degrees and greater than 135 degrees.

Additionally or alternatively, other methods of calculating approximations of the first and second off-resonant frequencies and phase differences $\omega1$, $\omega2$, $\phi1$, $\phi2$ can be employed such as, for example, fitting higher order polynomials, exponential curves, or the like, to two or more measured frequencies and phase differences. However, linear approximations may be desirably efficient, faster, or the like, when compared to alternative approximations.

The steps of measuring the first and second frequencies and corresponding phase differences and the calculation of a frequency and/or a phase difference, which may be linear approximations of the first and second off-resonant frequencies and phase differences $\omega1$, $\omega2$, $\phi1$, $\phi2$, can be performed within a desirable time frame. For example, because the frequency and phase difference can be determined without iterations of phase and frequency measurements, the vibration response parameters can be determined within a desirably short period of time. Accordingly, fluid properties, such as, for example, density and viscosity can be calculated and provided within a desirable time-frame.

Also, determining if the measured first and second phase differences are within a range, such as less than 135 degrees and greater than 45 degrees can be advantageous. For example, determining that the measured first and second phase differences are within the first and second off-resonant phase differences $\phi1$, $\phi2$ can prevent the inclusion of non-linear regions of, for example, the phase response plots 630, 640. Accordingly, the determined first and second off-resonant frequencies and phase differences $\omega1$, $\omega2$, $\phi1$, $\phi2$ may be more accurate.

Although the foregoing describes a non-iterative determination of the first and second off-resonant frequencies and phase differences $\omega1$, $\omega2$, $\phi1$, $\phi2$, the determination may be performed as part of an iterative process. For example, the determined first and second off-resonant frequencies and phase differences $\omega1$, $\omega2$, $\phi1$, $\phi2$ may be used as an estimate for a command frequency $\omega_c$ that is provided to the signal generator 147c in the open loop drive 147 described in the foregoing with reference to FIG. 4. Accordingly, the frequency of the drive signal may be about the actual first or second off-resonant frequencies and phase differences $\omega1$, $\omega2$, $\phi1$, $\phi2$ before iteration, thereby reducing the time required to measure the actual first and second off-resonant frequency $\omega1$, $\omega2$.

The detailed descriptions of the above embodiments are not exhaustive descriptions of all embodiments contemplated by the inventors to be within the scope of the present description. Indeed, persons skilled in the art will recognize that certain elements of the above-described embodiments may variously be combined or eliminated to create further embodiments, and such further embodiments fall within the scope and teachings of the present description. It will also be apparent to those of ordinary skill in the art that the above-described embodiments may be combined in whole or in part to create additional embodiments within the scope and teachings of the present description.

Thus, although specific embodiments are described herein for illustrative purposes, various equivalent modifications are possible within the scope of the present description, as those skilled in the relevant art will recognize. The teachings provided herein can be applied to other methods and apparatuses for determining a vibratory response parameter of a vibratory element, and not just to the embodiments described above and shown in the accompanying figures. Accordingly, the scope of the embodiments described above should be determined from the following claims.

We claim:

1. A method (900, 1000) of determining a vibration response parameter of a vibratory element (104), the method (900, 1000) comprising:
vibrating the vibratory element (104) at a first frequency with a first drive signal;
receiving a first vibration signal from the vibratory element (104) vibrated at the first frequency;
measuring a first phase difference, the first phase difference being a phase difference between the first drive signal and the first vibration signal;
vibrating the vibratory element (104) at a second frequency with a second drive signal;
receiving a second vibration signal from the vibratory element (104) vibrated at the second frequency;
measuring a second phase difference, the second phase difference being a phase difference between the second drive signal and the second vibration signal; and
using the first phase difference and the second phase difference to determine at least one of:
a phase difference; and
a frequency of the vibratory element (104).

2. The method (900, 1000) of claim 1, wherein the determined at least one of the phase difference and the frequency of the vibratory element (104) is a substantially linear approximation calculated from the first phase difference and the second phase difference.

3. The method (900, 1000) of claim 1, wherein the determined at least one frequency of the vibratory element (104) is one of a resonant frequency $\omega0$, a first off-resonant frequency $\omega1$, and a second off-resonant frequency $\omega2$ of the vibratory element (104).

4. The method (900, 1000) of claim 1, wherein the determined at least one phase difference is one of a resonant phase difference $\phi0$, a first off-resonant phase difference $\phi1$, and a second off-resonant phase difference $\phi2$.

5. The method (900, 1000) of claim 1, further comprising using the first phase difference and the second phase difference to calculate a linear approximation of a Q value of the vibratory element (104).

6. The method (900, 1000) of claim 1, wherein the determination of the at least one of the phase difference and the frequency of the vibratory element (104) is determined by one of a linear interpolation and a linear extrapolation.

7. The method (900, 1000) of claim 1, wherein the determined at least one of the phase difference and the frequency of the vibratory element (104) is used to calculate at least one of a viscosity and a density of a fluid measured by the vibratory element (104).

8. The method (900, 1000) of claim 1, further comprising determining if the first measured phase difference and the second measured phase difference is within a linear region of a phase response of a vibratory element (104).

9. A vibratory sensor (5) for determining a vibration response parameter of a vibratory element (104), the vibratory sensor (5) comprising:
a vibratory element (104) configured to be:
vibrated at a first frequency with a first drive signal;
vibrated at a second frequency with a second drive signal;

a meter electronics (20) communicatively coupled to the vibratory element (104) and configured to:
receive the first drive signal;
receive a first vibration signal from the vibratory element (104) vibrated at the first frequency; and
receive a second vibration signal from the vibratory element (104) vibrated at the second frequency;
measure a first phase difference, the first phase difference being a phase difference between the first drive signal and the first vibration signal;
measure a second phase difference, the second phase difference being a phase difference between the second drive signal and the second vibration signal; and
use the first phase difference and the second phase difference to determine at least one of:
a phase difference; and
a frequency of the vibratory element (104).

10. The vibratory sensor (5) of claim 9, wherein the determined at least one of the phase difference and the frequency of the vibratory element (104) is a substantially linear approximation calculated from the first phase difference and the second phase difference.

11. The vibratory sensor (5) of claim 9, wherein the determined at least one frequency of the vibratory element (104) is one of a resonant frequency $\omega 0$, a first off-resonant frequency $\omega 1$, and a second off-resonant frequency $\omega 2$ of the vibratory element (104).

12. The vibratory sensor (5) of claim 9, wherein the determined at least one phase difference is one of a resonant phase difference $\phi 0$, a first off-resonant phase difference $\phi 1$, and a second off-resonant phase difference $\phi 2$.

13. The vibratory sensor (5) of claim 9, wherein the meter electronics (20) is further configured to use the first phase difference and the second phase difference to calculate a linear approximation of a Q value of the vibratory element (104).

14. The vibratory sensor (5) of claim 9, wherein the meter electronics (20) is configured to determine the at least one of the phase difference and the frequency of the vibratory element (104) using one of a linear interpolation and a linear extrapolation.

15. The vibratory sensor (5) of claim 9, wherein the meter electronics (20) is further configured to calculate at least one of a viscosity and a density of a fluid measured by the vibratory element using the at least one of the phase difference and the frequency of the vibratory element (104).

16. The vibratory sensor (5) of claim 9, wherein the meter electronics (20) is further configured to determine if the first measured phase difference and the second measured phase difference is within a linear region of a phase response of the vibratory element (104).

* * * * *

UNITED STATES PATENT AND TRADEMARK OFFICE
CERTIFICATE OF CORRECTION

| | |
|---|---|
| PATENT NO. | : 10,527,534 B2 |
| APPLICATION NO. | : 15/529180 |
| DATED | : January 7, 2020 |
| INVENTOR(S) | : Craig B McAnally and Andrew S Kravitz |

Page 1 of 1

It is certified that error appears in the above-identified patent and that said Letters Patent is hereby corrected as shown below:

In the Specification

Column 9, Line 52, replace "$\phi 0$" with -- $\omega 0$ --

Signed and Sealed this
Ninth Day of June, 2020

Andrei Iancu
*Director of the United States Patent and Trademark Office*